United States Patent [19]

Lee

[11] Patent Number: 4,718,876
[45] Date of Patent: Jan. 12, 1988

[54] CHILD CALMING TOY WITH RYTHMIC STIMULATION

[76] Inventor: Min J. Lee, CPO Box 7068, Seoul, Rep. of Korea

[21] Appl. No.: 822,530

[22] Filed: Jan. 27, 1986

[30] Foreign Application Priority Data

Oct. 7, 1985 [KR] Rep. of Korea .................. 12993

[51] Int. Cl.⁴ ................................................ A61B 19/00
[52] U.S. Cl. ................................ 446/295; 128/1 C; 128/41
[58] Field of Search ............... 128/1 C, 41, DIG. 15; 446/295

[56] References Cited

U.S. PATENT DOCUMENTS

| | | | |
|---|---|---|---|
| 2,674,995 | 4/1954 | Marino | 128/41 |
| 2,742,037 | 4/1956 | Svoren | 128/41 |
| 2,757,480 | 8/1956 | Vchill | 446/295 |
| 2,954,642 | 10/1960 | Jackson | 446/295 |
| 3,110,980 | 11/1963 | Moormann | 446/295 |
| 3,119,200 | 1/1964 | Curtin et al. | 446/295 |
| 3,155,854 | 11/1964 | Stam | 128/41 |
| 3,298,132 | 1/1967 | Elwell | 446/295 |
| 3,563,229 | 2/1971 | Petrusson | 128/1 C |
| 3,888,233 | 6/1975 | Ware | 128/1 C |
| 4,576,150 | 3/1986 | Auracher | 128/DIG. 15 |

*Primary Examiner*—William E. Kamm
*Assistant Examiner*—Timothy Keegan
*Attorney, Agent, or Firm*—Handal & Morofsky

[57] ABSTRACT

A child calming device comprising, in accordance with the preferred embodiment, a stuffed animal (10) having a pocket (88) within which is contained a heart beat simulating transducer (12) is disclosed. The transducer is actuated by application of pressure to an actuator (22) which is coupled to a switch (30) which drives an electronic circuit (40) contained within the housing (14) of the simulator (12). The power of the "simulated" heart beats may be regulated by adjustment of a potentiometer via a knurled knob (98).

26 Claims, 8 Drawing Figures

CHILD CALMING TOY WITH RYTHMIC STIMULATION

TECHNICAL FIELD

The invention relates to pacification devices for children.

BACKGROUND ART

Over the years considerable technology has developed around the solution to the problem of pacifying babies and small children. Generally, infantile unrest and later, the hyperactivity of small children, are naturally occurring phenomena which, to greater and lesser extents, appear to be "programmed into" human beings from birth. In particular, the response of infants to the outside world appears to be calculated to stimulate the sort of parental attention which would certainly have been required in the relatively dangerous environment in which man evolved.

Thus the classic pattern appears. An abandoned child cries, signalling his mother to devote some attention to him either in the form of hugging, cuddling, nursing or the like. Upon the application of one of these stimuli, the crying usually stops.

Above and beyond this it has been found in research with the related species that withholding such stimuli can have permanent adverse effects on personality development and the mental stability of the adult animal. Controlled studies have shown, for example, that primates brought up in sterile laboratory surroundings without any objects around them have been found to be significantly disadvantaged as compared to other animals of the same species which were provided with a form which they could hug and which included structure which they could protect themselves in.

While such work is relatively recent, most successful infant pacifiers have always simulated otherwise naturally occurring human interactions. A few examples of such devices include milk bottles, nipple pacifiers, and soft dolls. In the case of somewhat older children one may also add pets and a different class of devices calculated to stimulate and interest the mind of the child. Such devices include crib chimes, animated dolls, talking dolls and the like.

While all of the above devices do perform the desired function of pacifying children, they all suffer from various inadequacies. For example, nipple pacifiers, while they are quite inexpensive and may intially be effective, do essentially frustrate the natural expectations of the infact and, after a short time, are recognized and rejected. Stuffed toy animals, while soft and appealing in texture, are essentially passive and thus, particularly in the case of infants, are not very effective as the infant is unable to fully comprehend the device. To a limited extent the device can be improved by incorporating an audio device (such as a tape recorder) in a toy doll to add an audio stimulus to such a pacifier. However, the stimulus is extremely complicated and not of a type likely to be understood or learned by a small infant. In addition, in the case of smaller children, talking dolls are likely to have the opposite of the desired effect, that is stimulating activity, instead of providing a calming influence. In addition, such talking dolls are likely to be expensive and complicated devices which are highly subject to breakdowns and sensitive to the abuse likely to be given to them by children.

DISCLOSURE OF INVENTION

The invention, as claimed, is intended to provide a remedy. It solves the problem of how to provide a pacifier for infants and small children which is simple, inexpensive, and effective. Generally this is achieved by providing a soft, huggable and pleasantly textured object, such as a teddy bear, with an audio cue of a simple periodic nature which is capable of being understood and anticipated by even very small infants and, in the case of small children, is identifiable with life functions of a real parent, companion or pet. In accordance with the preferred embodiment of the invnention, the pacifier comprises a stuffed animal with an electronic heart beat mimicking device.

BRIEF DESCRIPTION OF DRAWINGS

One way of carrying out the invention is described in detail below with reference to drawings which illustrate only specific embodiments of the invention, in which.

BEST MODE FOR CARRYING OUT THE INVENTION

Figure 1:
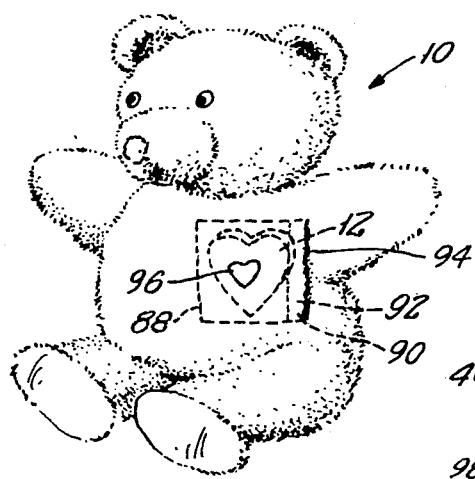
FIG. 1 is a perspective illustrating the position of a heart-beat simulator contained within the inventive toy.
Figure 2:
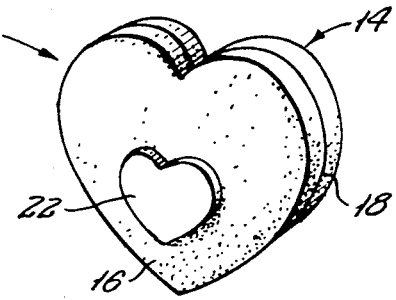
FIG. 2 is a perspective view of the simulator.
Figure 3:
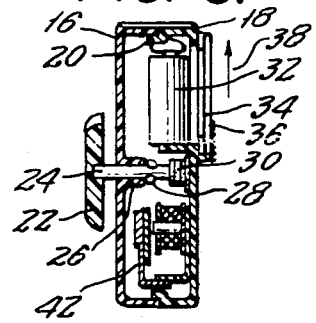
FIG. 3 is a cross sectional view along lines 3—3 of FIG. 2.

Referring first to FIGS. 1-2, the preferred embodiment of the invention is directed to dolls and toy animals including a subsystem which provides the impression of actual heart beats. It is believed that a doll, such as toy animal or teddy bear 10, with a heart-beat simulator 12 will induce in the person playing with it feelings of contentment, warmth and comfort, and aesthetic satisfaction similar to those he would experience if he were handling or being played with by a living person. Housing 14 comprises a front cover 16 and a rear cover 18 which may engage each other via an overhanging edge 20 on the rear cover as illustrated in FIG. 3. As can be seen most clearly in FIGS. 2 and 3 a heart shaped push button actuator 22 is slidingly mounted in the front cover 16 for movement toward and away from rear cover 18. This movement is achieved by providing a support pin 24 which is secured to actuator 22 and slides in a sleeve 26 which is secured to and integral with front cover 16. Actuator 22 together with support pin 24 is prevented from falling out from housing 14 by a stop member 28 which is integral with pin 24.

As can be seen most clearly in FIG. 3, support pin 24 directly overlies a switch 30 which is wired to actuate an electronic pulsing circuit powered by a battery 32. Replacement of worn batteries is accommodated by a slide battery cover 34 of conventional design and which incorporates gripping surface 36. Cover 34 is configured to be slidingly removed in the direction indicated by arrow 38 upon the application of appropriate pressure to gripping surface 36. Finally, the housing contains an electronic pulsating circuit 40 and a heart beat simulating transducer 42.

Figures 5, 6:
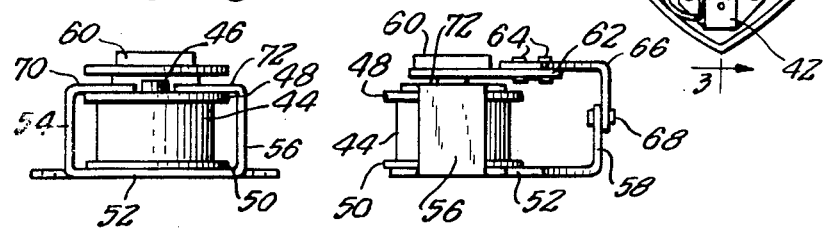
FIG. 5 is a is a plan view of the heart beat transducer.
FIG. 6 is a plan view along lines 6—6 of FIG. 5.

Transducer 42, as shown in FIG. 5-6, comprises an electromagnet 44 which includes a core 46 around which the windings of electromagnet 44 are wound. The windings are confined by a pair of spool ends 48 and 50 which serve as a means for securing electromagnet 44 to a support 52. Support 52 is made from a generally T-shaped sheet of ferromagnetic material such as steel. The sheet is bent to form a pair of magnetic flux conducting members 54 and 56 and a spring support 58 (FIG. 6).

Electromagnet 44 actuates a ferromagnetic bob 60 which is mounted on a ferromagnetic strip 62 by epoxy or any other suitable adhesive. Strip 62, in turn, is riveted by rivets 64 to spring 66 which, in turn, is riveted by rivets 68 to support 58. The spring constant of spring 66 is such that upon the application of a pulse to electromagnet 44, bob 60 will be attracted toward but will not make clicking contact with the top surfaces 70 and 72 of members 54 and 56.

Figure 7:
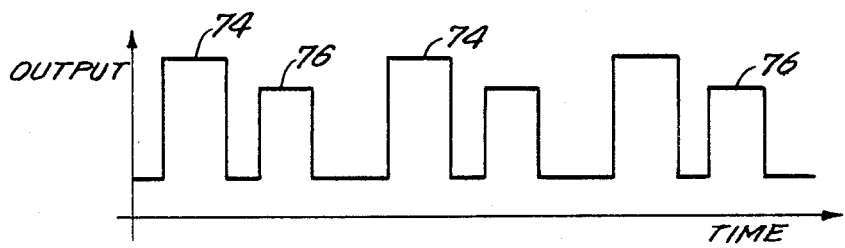
FIG. 7 is a graph of the excitation voltage to the transducer.

A typical driving voltage is illustrated in FIG. 7. As can be seen from FIG. 7, the pulses alternate between a higher amplitude pulse 74 having a relatively low frequency content and a smaller amplitude pulse 76 having a relatively high frequency content, as illustrated in FIG. 7. As these pulses are applied to transducer 42, which in turn deflects the mass of bob 60 and results in causing relative movement of housing 14 with respect to bob 60, the impression of a beating heart is given by heart shaped housing 14 which vibrates backwards and forwards in the chest of bear 10.

Figure 4:
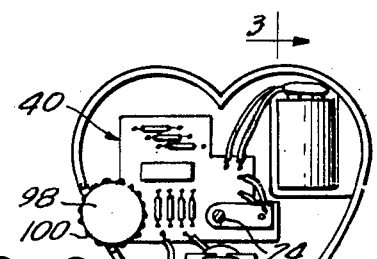
FIG. 4 is a view of the vibrator circuit of the simulator.
Figure 8:
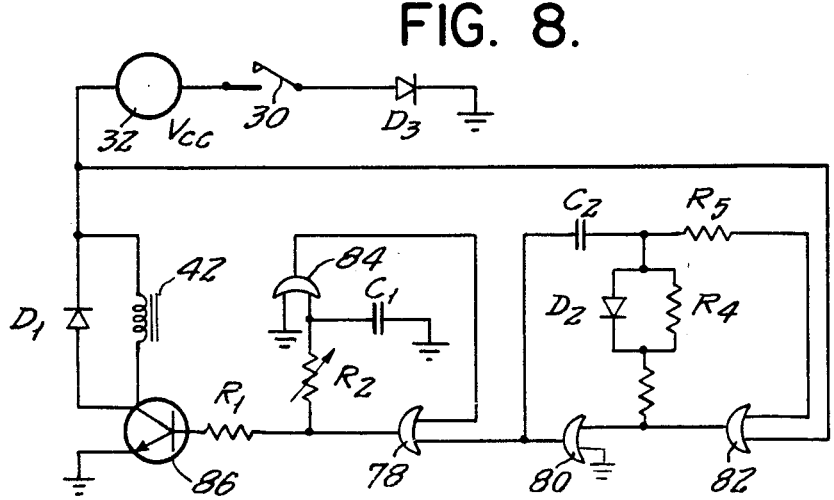
FIG. 8 is a schematic of the vibrator circuit that outputs the waveform of FIG. 7 to the transducer.

Although many electronic circuits are capable of producing a suitable pulse train such as that illustrated in FIG. 7 or other pulse trains which will also provide a heart beat simulation, by way of illustration one such circuit will be described in conjunction with FIG. 8. In particular, the device comprises a number of gates 78, 80, 82 and 84. These gates together with a transistor 86 form a circuit for driving transducer 42. Actuation of the electronic circuit is achieved by closing of switch 30 which is illustrated in FIGS. 3, and 4 and, in schematic form, in FIG. 8.

The electrical values or catalog numbers of the various electrical elements described above are:

$V_{cc}$: 9 Volt Battery
$D_1$, $D_2$, $D_3$: 1N 4148 diodes
$R_1$: 2.2 Kilohm resistor
$R_2$: 300 Kilohm variable resistor
$R_3$: 1.5 Megohm resistor
$R_4$: 4.7 Megohm resistor
$R_5$: 1 Megohm resistor
$C_1$: 0.0068 microfarad capacitor
$C_2$: 0.0047 microfarad capacitor When it is desired to use the inventive child pacifying device, the simulator 12 is provided with a battery 32 by removal of slide battery cover 34 which, after insertion of the battery is put back on the housing. The simulator 12 is then placed in a pocket 88 which is sewn into bear 10. Pocket 88 is closed by mating Velcro strips 90 and 92 which are contained within the pocket just inside its opening 94. After the pocket is closed by bringing Velcro strips 90 and 92 into contact with each other, the teddy bear is then ready to be enjoyed by the child. If desired an outer heart 96 may be sewn to the body of the teddy bear to cause a child to associate the heart beat with, for example, an applique heart 96. In the alternative applique heart 96 may be sewn to an item of clothing to be worn by the bear 10.

When the child either hugs the bear or feels its heart, it causes actuator 22 to drive pin 24 toward switch 30 closing the electrical circuit and commencing the generation of the pulses illustrated in FIG. 7 to the transducer illustrated in FIGS. 5 and 6. As discussed above, this results in the perception of a pulsating heart within toy bear 10.

If desired, it is possible to regulate the strength of the heart beats in accordance with the power of the battery or, perhaps, the desire to minimize the strength of the heart beat to allow a particular child to sleep by regulation of the value of variable resistor $R_2$ to by rotation of a knurled knob 98 which includes serrations 100 to allow for easy rotation of the same. Naturally, whenever the child stops hugging bear 10 perhaps because it has fallen asleep or has stopped playing with the bear, the push button switch 30 automatically springs back to the unactuated position, thus conserving power in the battery.

While an illustrative embodiment of the invention has been described, it is, of course, understood that various modifications of the invention will be obvious to those of ordinary skill in the art. Such modifications are within the spirit and scope of the invention which is limited and defined only by the appended claims.

I claim:

1. A child pacifying doll, comprising:
   (a) a skin defining doll body configured and dimensioned to allow the doll body to be hugged;
   (b) stuffing means disposed in said skin, and filling said skin into a soft doll body form and defining an internal volume within said doll body;
   (c) a vibrator element having a mass, disposed in said internal volume; and
   (d) an electromagnetic inertial pulsating device secured to said vibrator element, said inertial device having a vibrating mass coupled resiliently to the mass of the vibrator element and comprising switch means for sensing the proximity of a child and pulsating in response thereto.

2. A child pacifying doll as in claim 1, wherein said vibrator element is a vibrator casing and said electromagnetic device is disposed within said casing.

3. A doll as in claim 2 wherein said volume communicates with the ambient through a port defined by the outer surface of said body and further comprising closure means secured around said port for closing said volume.

4. A doll as in claim 3 wherein said port has two overlying sides and said closure means comprises a pair of mating Velcro-type strips disposed on opposite overlying sides of said port through which said volume communicates with the outside of said volume, said strips being positioned not to be visible from the outside of said body when said opening is closed with said strips in overlying positions in engagement with each other.

5. A doll as in claim 2 wherein said switch means actuates said pulsating device in response to the application of an object to the outer surface of said doll body.

6. A doll as in claim 5 wherein said skin has an inside surface and said switch means comprises a push button which extends from said pulsating device and bears against said inside surface of said skin.

7. A doll as in claim 2 wherein said electromagnetic device comprises an electronic driver which is turned on and off by said switch means which is positioned to be actuated upon application of hugging pressure around said doll body.

8. A doll as in claim 2 wherein said switch means comprises a push button switch positioned to be actuated upon hugging of the doll body and wherein said push-button switch actuates an electronic driver which drives said electromagnetic device and wherein said electronic driver outputs a series of electrical pulses.

9. A doll as in claim 8 wherein said pulses alternate between a strong pulse and a relatively weak pulse.

10. A doll as in claim 8 wherein said pulses alternate between pulses of relatively high frequency content and relatively low frequency content.

11. A doll as in claim 8 wherein said pulses comprise a series of two pulse groups, each of said pulse groups beginning with a relatively high amplitude and low frequency content pulse followed by a relatively low amplitude and high frequency content pulse.

12. A doll as in claim 2, wherein said pulsating device is actuated by electrical pulses and further comprising means to vary the amplitude of said electrical pulses.

13. A doll as in claim 2, wherein said electromagnetic device comprises a resilient member securing said vibrator element to said vibrating mass and means for displacing two ends of said member with respect to each other to extreme relatively close positions relative to each other where the two ends are still spaced apart from each other whereby displacement occurs without impact.

14. A doll is in claim 13, wherein said resilient member comprises a U-shaped leaf spring.

15. A child pacifying doll, comprising:
(a) a soft doll body;
(b) pocket means associated with said body and defining a volume in said body, said pocket means opening to the outer surface of said body;
(c) a casing disposed within said volume;
(d) a vibrating member associated with said casing;
(e) an electromagnet disposed in said casing;
(f) a leaf spring for securing said electromagnet to said vibrating member at a position where said vibrating member is displaced by actuation of said electromagnet, said electromagnet and said vibrating member forming a pulsation assembly; and
(g) means for securing said assembly to said casing.

16. A doll as in claim 15 wherein said pocket communicates with the ambient through a pocket opening and said opening may be closed by a pair of mating Velcro-type strips contained on opposite sides of said opening and positioned not to be visible from the outside of said body when said opening is closed.

17. A doll as in claim 16 further comprising switch means for actuating said pulsating device upon the application of pressure to the outer surface of said doll body.

18. A doll as in claim 17, wherein said switch is a push-botton switch which extends from the front of said casing.

19. A doll as in claim 18 wherein said doll body comprises an outer skin made of plush material and a soft fibrous stuffing.

20. A child pacifying doll, comprising:
(a) a soft doll body;
(b) means defining an internal compartment in said body;
(c) a bob weight disposed in said compartment;
(d) magnetic means disposed in said compartment;
(e) a leaf spring for securing said magnetic means to said bob weight at a position to be displaced by said magnetic means;
(f) drive circuit means for applying pulses of electrical energy to said magnetic means sufficient to displace said bob weight with respect to said magnetic means only to extreme positions relative to each other where the two are still spaced apart from each other whereby movement occurs without impact; and
(g) battery power supply means for powering said drive circuit means, said power supply means being positioned, configured, and dimensioned to be replaceable without destruction of any part of said doll.

21. A doll as in claim 20, wherein said body simulates a living being.

22. A doll as in claim 21, wherein said living being is an animal.

23. A doll as in claim 22 wherein said animal is a bear.

24. A child pacifying doll, comprising:
(a) a skin defining a doll body;
(b) stuffing means disposed in said skin, and filling said skin into a soft doll body form and defining an internal volume within said doll body;
(c) a vibrator element disposed in said internal volume; and
(d) an electromagnetic inertial pulsating device secured to said vibrator element, said inertial device comprising:
(i) a vibrating mass;
(ii) spring means for coupling said vibrating mass resiliently to the vibrator element;
(iii) electromagnetic means for displacing said vibrating mass with respect to said vibrator element;
(iv) drive means for pulsing said electromagnetic means to cause pulsation of said pulsating device with pulses strong enough to cause said vibrating mass to move with respect to said vibrator element but not strong enough to cause said vibrating mass to experience impact; and
(v) switch means for turning on said drive means.

25. A child pacifying doll as in claim 24, wherein said doll body is configured to be hugged.

26. A child pacifying doll as in claim 24, wherein said element is a casing and said switch means is a push switch extending from said casing.

* * * * *